United States Patent [19]

Kukes et al.

[11] Patent Number: 4,513,099

[45] Date of Patent: Apr. 23, 1985

[54] OLEFIN METATHESIS AND CATALYST

[75] Inventors: Simon G. Kukes; Robert L. Banks, both of Bartlesville, Okla.

[73] Assignee: Phillips Petroleum Company, Bartlesville, Okla.

[21] Appl. No.: 584,220

[22] Filed: Feb. 27, 1984

Related U.S. Application Data

[62] Division of Ser. No. 518,557, Jul. 29, 1983, Pat. No. 4,465,891.

[51] Int. Cl.$^3$ .......................... B01J 27/00; B01J 27/10
[52] U.S. Cl. .................................. 502/228; 502/224; 502/241; 502/254; 502/255
[58] Field of Search ............... 502/228, 224, 241, 254, 502/255

[56] References Cited

U.S. PATENT DOCUMENTS

| | | | |
|---|---|---|---|
| 3,365,513 | 1/1968 | Heckelsberg | 502/255 X |
| 3,544,647 | 12/1970 | Pennella | 260/683 |
| 3,761,427 | 9/1973 | Regier | 502/228 |
| 3,915,897 | 10/1975 | Reusser et al. | 502/241 |
| 3,974,100 | 8/1976 | Kubicek | 502/255 X |
| 4,215,017 | 7/1980 | Reusser et al. | 502/254 X |
| 4,368,345 | 1/1983 | Dickinson | 502/254 X |

OTHER PUBLICATIONS

Journal of Catalysis, 34, pp. 52–56, (1974), Pennella et al.

*Primary Examiner*—Patrick Garvin
*Attorney, Agent, or Firm*—Howard D. Doescher

[57] ABSTRACT

Olefins are converted into other olefins having different numbers of carbon atoms by contact with a catalyst produced by combining a metal, such as tungsten or a tungsten compound, with a halosilane by adding either water or silica to the suspension of metal and halosilane and then heating to activate the catalyst.

12 Claims, No Drawings

OLEFIN METATHESIS AND CATALYST

This is a divisional application of Ser. No. 518,557, filed July 29, 1983, now U.S. Pat. No. 4,465,891.

BACKGROUND OF THE INVENTION

This invention relates to the disproportionation (metathesis) of olefins. In accordance with one aspect, this invention relates to a catalyst suitable for use in the disproportionation of olefinic hydrocarbons. In accordance with another aspect, this invention relates to a process for the disproportionation of olefinic hydrocarbons. In accordance with a further aspect, this invention relates to a catalyst suitable for use in the disproportionation of olefins comprising at least one of tungsten, molybdenum and rhenium, and silicon. In accordance with a further aspect, this invention relates to a catalyst suitable for use in the disproportionation of olefins comprising a metal active for disproportionation and silicon prepared by combining the metal or a metal compound with a halosilane solvent and activating. In accordance with another aspect, this invention relates to a process for the disproportionation of olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Many catalysts have been developed for disproportionation such as those comprising inorganic, refractory oxides containing a catalytic amount of a metal or metal oxide. The present invention is based upon the discovery of a way to improve the activity of such catalysts.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms than the feed hydrocarbons.

Still another object is to provide a method for improving the activity of a tungsten catalyst for the conversion of olefins into olefins having different numbers of carbon atoms than the feed hydrocarbons.

Other aspects, objects and the several advantages of the invention will be apparent to one skilled in the art upon reading the disclosure, including a detailed description of the invention and the appended claims.

SUMMARY OF THE INVENTION

In accordance with the present invention, a disproportionation (metathesis) catalyst comprising a metal active for disproportionation such as tungsten, molybdenum and rhenium, and silicon is prepared by combining the metal or a metal compound thereof with a halosilane compound followed by activating to produce a catalyst effective for the metathesis of olefins.

In accordance with one embodiment of the invention, an olefin metathesis catalyst is prepared by (a) combining at least one of tungsten, molybdenum and rhenium with a halosilane, such as hexachlorodisilane or hexachlorodisiloxane, followed by (b) addition of water to hydrolyze and polymerize the halosilane, and (c) calcining the product of (b) to produce a catalyst active for the metathesis of olefins.

In accordance with another embodiment of the invention, an olefin metathesis catalyst comprising a metal active for disproportionation is prepared by combining a support, such as silica, with a halosilane, e.g., hexachlorodisilane or hexachlorodisiloxane, with a solution of a metal compound, such as $WCl_6$, and heating under suitable conditions to remove excess solvent and form an active metathesis catalyst.

More specifically, and a presently preferred embodiment, a disproportionation catalyst comprising tungsten is prepared by (a) combining tungsten or tungsten hexachloride ($WCl_6$) with hexachlorodisilane, ($Si_2Cl_6$) (b) adding either water or silica to (a), and (c) heating (b) to dry and/or activate the tungsten-containing catalyst.

Also, according to the invention, a process is provided for the disproportionation of an acyclic olefinic hydrocarbon feed by contacting the same with a disproportionation catalyst as hereinbefore described under conditions of temperature and pressure which effect disproportionation of the feed.

DESCRIPTION OF PREFERRED EMBODIMENTS

The catalysts which are useful for the present invention are those which have activity for the disproportionation of olefins such as propylene into ethylene and butenes, a preferred catalyst comprises tungsten and silicon. It is within the scope of the invention to utilize other metals known to be active for disproportionation individually or in combination with tungsten, such as molybdenum, rhenium, and the like. It is further within the scope of the invention to use organic refractory oxide supports in combination with the catalysts of the invention.

For purposes of this application, the term "halosilane" is intended to include halosiloxanes.

In accordance with the invention, at least one of tungsten, molybdenum, and rhenium or a suitable compound thereof, such as tungsten hexachloride, is combined by suspending in a suitable halosilane particularly a halodisilane or halodisiloxane, preferably hexachlorodisilane or hexachlorodisiloxane. Other metal compounds that can be used include carbonyls, carbides, and sulfides as well as the hexachlorides.

The proportion of the metal combined with the support can vary appreciably but generally the support will contain at least about 0.1% by weight of the metal, calculated as the oxide with amounts of from about 0.2 to about 40% by weight being preferred and about 2 to about 20% by weight, especially preferred. The weight percent referred to is based on the combined weights of the support and the metal, e.g. tungsten, molybdenum, and rhenium.

The amount or ratio of metal to halosilane in the catalyst will generally range from about 0.1 to 50 weight percent, preferably about 1 to about 20 weight percent. The amount or ratio of halosilane to support will generally range from 0 to about 1,000 weight percent, preferably 0 to about 200 weight percent.

The suspension of tungsten and halosilane can be combined with either water or silica followed by activation to form the catalyst of the invention. The addition of water to the suspension hydrolizes and polymerizes the halosilane. In this embodiment of the invention, the catalyst is calcined after water addition at an elevated temperature in the presence of an oxygen-containing gas to produce an active disproportionation catalyst.

The amount of water added to the suspension of metal or metal compound and halosilane will be sufficient to cause hydrolysis and polymerization of the halosilane to form a solid material ready for activation. In general, the amount of water employed will range from about 50 to about 200 volume percent based on the amount of halosilane.

In another embodiment of the invention the suspension of metal or metal compound and halosilane is combined with silica ($SiO_2$) to form a metal/silica-containing disproportionation catalyst composition. In this embodiment the catalyst is ordinarily activated by heating at an elevated temperature above about 200° C. in the presence of an inert gas under conditions which are sufficient to remove solvent from the catalyst and provide an active form of the catalyst composition.

As noted hereinbefore, it is within the scope of the invention to include other support materials along with silica when combining with the suspension of metal or metal compound and halosilane. Suitable support materials which can be combined with the metals or metal compounds active for disproportionation according to the invention include alumina, silica, silica-alumina, magnesia-titania, thoria, aluminum phosphate, zirconium phosphate, titanium phosphate, calcium phosphate, magnesium phosphate, and the like, and mixtures thereof.

If desired excess halosilane can be removed from the catalyst suspension by washing with a hydrocarbon such as the alkanes, for example, hexane, heptane and the like. The catalyst can then be dried by heating at an elevated temperature of say about 200° C. or higher by passage of an inert gas such as nitrogen over the catalyst. This can be accomplished within the reactor or in other suitable catalyst preparation equipment.

Calcination when used, is conducted by heating the metal/silicon-containing catalyst in the presence of an oxygen-containing gas, such as air, under conditions sufficient to convert the metal or metal compound and silicon compounds present to the oxides. Temperatures in the range of about 350° C. to about 800° C. are generally satisfactory for such calcination. The time for subjecting the catalyst to calcination is sufficient to activate the catalyst. Typically less time is required at higher temperatures and vice versa. If desired the thus calcined catalyst can be further treated with an inert gas such as nitrogen prior to use in the disproportionation reaction.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom. Internal olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The reaction temperature can vary depending upon the catalyst and feed(s) employed. Typically the disproportionation is carried out at a temperature in the range of about 0° to about 600° C., preferably from about 20° to about 500° C.

The disproportionation reaction can be carried out by contacting the olefins to be disproportionated with the catalyst in the liquid phase or the gas phase depending on structure and molecular weight of the olefin. Pressure during the disproportionation reaction can vary between wide limits. For example, pressures between 0.1 and 500 atmospheres are suitable, although preferred pressures are between about 1 and 40 atmospheres.

If the reaction is carried out in the liquid phase, solvents or diluents for the reactants can be used. Aliphatic saturated hydrocarbons e.g., pentane, hexanes and cyclohexane, dodecane and aromatic hydrocarbons such as benzene and toluene are suitable. If the reaction is carried out in the gaseous phase diluents such as aliphatic hydrocarbons for example, methane, ethane, and/or substantially inert gases, e.g. nitrogen, argon, can be present. Preferably, the disproportionation reaction is effected in the absence of significant amounts of deactivating materials such as water and oxygen.

The contact time needed to obtain a reasonable yield of disproportionated products depends upon several factors such as the activity of the catalyst, temperature, pressure and structure of the olefinically unsaturated compound to be disproportionated. Length of time during which the olefinic unsaturated compounds to be disproportionated are contacted with the catalyst can conveniently vary between 0.1 seconds and 24 hours although longer and shorter contact times can be used. Preferably, times of about 1 second to about 1 hour are used.

The process of the invention can be effected batchwise or continuously with fixed bed catalyst beds, slurried catalyst, fluidized beds, or by using any other conventional contacting techniques.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processed to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

All runs were made by passing a propylene feed through a vertical tubular quartz reactor (1 cm in diameter and 25 cm in length) positioned in a temperature-controlled electric furnace. In each run the reactor contained a bed of the designated catalyst. A thermocouple was positioned in the catalyst bed to monitor reaction temperature. Prior to each run the catalyst was activated by heating at 200° C.–600° C. in flowing nitrogen for 0.5 hours. Regeneration, when indicated, was accomplished with flowing air at 600° C. for one hour, followed by a nitrogen flush at 600° C.

The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor. Reaction product analyses were made by gas-liquid chromatography (glc) employing a Hewlett-Packard model 5880A chromatograph having a ⅛ inch by 20 ft. column packed with 19% Bis-2-methoxyethoxyethylene (BMEE)+1% on 60/80 Chrom P. Analysis was carried out isothermally at a temperature of 30° with a helium carrier gas flow rate of about 20 mL/min.

EXAMPLE I

Catalyst Preparations

The tungsten oxide content of control Catalyst A was 6 weight percent based on the total weight of tungsten oxide and silica. Control Catalyst A was prepared by impregnating high surface area silica with 0.0727 gram of ammonium metatungstate $((NH_4)_2W_4O_{13} \cdot 8H_2O)$ per gram of silica. The impregnation was accomplished by treating the silica with an aqueous solution of ammonium metatungstate. The impregnated silica was dried and calcined in air at 500° C. to convert the metatungstate to the oxide. A $-20+40$ mesh sieve fraction was obtained for use as described below.

Control catalyst B was prepared by dissolving 0.2 g of $WCl_6$ in 4 mL of benzene in a ceramic dish under a nitrogen atmosphere. The solution was stirred with a glass rod while 2.6 g of 20–40 mesh $SiO_2$ (Davison) was added. Catalyst was dried by continuing to blow nitrogen over the dish contents until essentially all benzene was removed. The catalyst was loaded into the metathesis reactor and heated to 200° C. under a nitrogen flow for 2.5 hours. Catalyst thus prepared was ready for propylene feed.

Control catalyst C was prepared employing Davison 20–40 mesh $SiO_2$ which had been heated for one hour at 550° C. in air, followed by one hour at the same temperature under nitrogen. A 3 g aliquot of the $SiO_2$ so treated was added to 15 mL of dry benzene containing 0.2 g $WCl_6$. Nitrogen was passed over the catalyst until all benzene was removed. The catalyst was then placed in the metathesis reactor, heated to 200° C. for 3 hours under a nitrogen flow. Catalyst so prepared was then ready for propylene feed.

Invention catalyst D was prepared by dissolving 0.2 g of $WCl_6$ in 3 mL of $Si_2Cl_6$ in a ceramic dish under a nitrogen atmosphere. To this, 2.6 g of 20–40 mesh Davison $SiO_2$ was added. Solvent was removed by blowing across the dish contents with a strong nitrogen stream. Hexane was then added, dish contents stirred, solvent decanted and catalyst again dried by passing a vigorous $N_2$ stream over the dish contents. Catalyst was then placed in the metathesis reactor, heated to 200° C. under a nitrogen flow for about 2.5 hours, then cooled to 150° C. to begin testing for metathesis activity by introducing propylene feed.

Invention catalyst E was prepared by suspending 0.8 g of $WCl_6$ in 9 mL of $Si_2Cl_6$ in a ceramic dish under a nitrogen atmosphere. While stirring of this suspension with a glass rod was maintained, 8 g of 20–40 mesh $SiO_2$ (Davison Grade) was added. A nitrogen stream was passed over the dish contents to aid drying, an aliquot of hexane (about 5 mL) added, then decanted, then the nitrogen flow continued at room temperature to aid drying the catalyst. Catalyst was then placed in the metathesis reactor, heated to 200° C. under a nitrogen flow for about 2.5 hours, then cooled to 150° C. to begin testing for metathesis activity by introducing propylene feed.

Invention catalyst F was prepared employing $SiO_2$ support pre-calcined as described in the preparation of control catalyst C. Thus, 0.2 g of $WCl_6$ suspended in 5 mL of $Si_2Cl_6$ was poured over 3 g of the calcined $SiO_2$ while still in the reactor under a nitrogen atmosphere. Catalyst was then washed with about 10 mL of heptane to remove unreacted $Si_2Cl_6$, then dried by heating to about 200° C. for about 3 hours under a nitrogen flow. Catalyst was then ready for introduction of propylene feed.

Invention catalyst G was prepared by suspending 0.2 g of metallic tungsten in 3 mL of $Si_2Cl_6$ in a ceramic dish. This suspension was stirred with a glass rod while 3 mL of water were added over about 1 minute. The heat evolved upon water addition was sufficient to produce an essentially dry catalyst by the time water addition was complete. Catalyst was loaded into the metathesis reactor and activated under an air flow at 550° C. for 1.5 hour, then purged under nitrogen flow for 30 minutes at the same temperature. Catalyst was then cooled to 450° C. and ready for propylene feed.

EXAMPLE II

Metathesis Reactions

The catalysts prepared as described above were subjected to propylene feed at atmospheric pressure to determine metathesis activity at a variety of reaction temperatures. In several cases, after the initial catalyst activity was determined, catalyst was subjected to calcination conditions of 450°–650° C., then purged with nitrogen and again tested for metathesis activity. Reaction conditions and analytical results employing each catalyst described above are presented in the Table.

| NB | Run | Catalyst, g | Propylene flow, mL/min | Reaction temp, °C. | Propylene conversion, % time on stream minutes | | | | |
|---|---|---|---|---|---|---|---|---|---|
| | | | | | 5 | 15 | 30 | 60 | 90 |
| 27451-12 | 1 | A, 1.5 | 150 | 400 | 13.7 | 14.3 | 16.3 | 18.0 | 17.8 |
| 27066-34 | 2* | A, 1.5 | 100 | 400 | 14.9 | — | 10.1 | 9.9 | — |
| 27042-52 | 3 | B, 2.6 | 140 | 200 | <0.1 | <0.1 | — | — | — |
| | 4 | | 140 | 250 | <0.1 | <0.1 | <0.1 | — | — |
| | 5 | | 140 | 400 | — | — | ≧0.5 | — | — |
| | 6 | | 140 | 450 | — | — | ≧1 | — | — |
| 27042-53 | 7 | C, 3.0 | 140 | 200 | <0.1 | <0.1 | <0.1 | — | — |
| | 8 | | 140 | 250 | — | — | <0.5 | — | — |
| | 9 | | 140 | 300 | 0.4 | 3.6 | 18.2 | 41.8 | 42.9 |
| | 10 | | 140 | 200 | 26.2 | 15.9 | 12.9 | 11.6 | — |
| 27042-49 | 11 | D, 2.6 | 140 | 150 | 10.5 | 10.4 | — | — | — |
| | 12 | | 140 | 200 | 38.4 | 40.3 | 40.8 | 40.9 | 40.0 |
| -50 | 13** | | 140 | 150 | — | — | <0.1 | — | — |
| | 14 | | 140 | 200 | — | — | <0.1 | — | — |
| | 15 | | 140 | 250 | — | — | <0.1 | — | — |
| | 16 | | 140 | 400 | — | — | <0.1 | — | — |
| -51 | 17*** | | 140 | 400 | 13.4 | 39.7 | 40.8 | 42.5 | 42.4 |
| -51 | 18**** | | 140 | 400 | 14.3 | 17.8 | 19.3 | 19.2 | 18.3 |
| 27284-1 | 19 | E, 1.7 | 180 | 195 | 25.4 | — | 28.2 | 26.3 | 23.5 |
| 27042-55 | 20 | F, 3.0 | 140 | 200 | 3.3 | 9.2 | 15.2 | 17.4 | 17.5 |
| | 21 | | 140 | 300 | 31.8 | 41.5 | 45.3 | 45.3 | — |
| 27042-47 | 22 | G, 1.4 | 150 | 450 | 2.7 | 4.8 | 6.2 | 8.1 | 9.4 |
| | 23*** | | 150 | 412 | 0.6 | 1.3 | 1.7 | 2.3 | — |

*Catalyst heated to 650° C. in air for 10 minutes; purged with nitrogen for 10 minutes, then cooled to reaction temperature.
**Catalyst heated to 450° C. for 1 hour; purged with $N_2$ for 30 minutes, then cooled to reaction temperature.
***Catalyst heated to 550° C. for 2 hours; purged with $N_2$ for 30 minutes, then cooled to reaction temperature.
****Catalyst heated to 600° C. for 2 hours; purged with $N_2$ for 30 minutes, then cooled to reaction temperature.

The results of these experiments demonstrate that catalysts prepared according to this invention exhibit high metathesis activity at relatively low reaction temperatures. For example, control catalyst B displays essentially no metathesis activity at 200° C., while invention catalyst D provides measurable activity at temperatures as low as 150° C., with conversion at 200° C. of about thermodynamic equilibrium. Although invention catalyst D appears to lose its low temperature activity upon calcination treatment at 550° C., it still displays excellent conversions at 400° C. (see run 17). Note that control catalyst C is active at 200° C. only after being pre-conditioned under a propylene flow at 300° C. (see run 9). In addition, the pre-conditioned catalyst appears to rapidly lose low temperature activity (run 10).

Invention catalysts E and F display significant metathesis activity at relatively low temperatures.

That which is claimed:

1. A composition suitable for the disproportionation of olefins comprising silicon and at least one metal selected from tungsten, molybdenum, and rhenium produced by
   (a) combining the metal or metal compound with a halosilane compound
   (b) adding either water or silica to (a), and
   (c) heating (b) to activate and form a metal/silicon-containing catalyst active for the disproportionation of olefins.

2. A composition according to claim 1 wherein (b) comprises the addition of sufficient water to (a) to hydrolize and polymerize said halosilane and said heating in (c) is carried out under calcination additions comprising an elevated temperature and a sufficient amount of oxygen-containing gas to calcine and activate catalyst.

3. A composition according to claim 1 wherein (b) silica ($SiO_2$) is combined with (a) and (c) the product of (b) is heated in (c) under conditions including an inert gas and an elevated temperature sufficient to form a metal/silicon catalyst effective for disproportionation of olefins.

4. A composition according to claim 1 wherein the halosilane is a halodisilane or halodisiloxane compound and said metal is tungsten.

5. A composition according to claim 4 wherein tungsten or tungsten hexachloride is combined with hexachlorodisilane in (a).

6. A composition according to claim 1 wherein the amount of metal, calculated as the metal oxide, in the catalyst ranges from about 0.1 to about 40 weight percent based on total weight of catalyst.

7. A composition according to claim 1 which additionally includes at least one other metal active for disproportionation in addition to tungsten.

8. A composition according to claim 7 which additionally contains a refractory inorganic oxide support material other than silica.

9. A composition according to claim 4 wherein (b) comprises the addition of sufficient amount of water to (a) to hydrolize and polymerize said halosilane and said heating in (c) is carried out under calcination conditions comprising an elevated temperature and a sufficient amount of oxygen-containing gas to activate said catalyst.

10. A composition according to claim 4 wherein silica ($SiO_2$) is combined with (a) and in (b), the product of (b) is heated in (c) under conditions comprising an elevated temperature in the presence of an inert gas sufficient to form a tungsten/silicon catalyst effective for disproportionation of olefins.

11. A composition according to claim 2 wherein said temperature of calcination is at least about 200° C. and is carried out in the presence of air.

12. A composition according to claim 3 wherein the heating in (c) is carried out at a temperature of at least about 200° C. in the presence of an inert gas.

* * * * *